(12) United States Patent
Carter

(10) Patent No.: US 7,249,949 B2
(45) Date of Patent: Jul. 31, 2007

(54) INTERNAL CONNECTION DENTAL IMPLANT

(75) Inventor: Robert D. Carter, Apple Valley, MN (US)

(73) Assignee: Lifecore Biomedical, Inc., Chaska, MN (US)

( * ) Notice: Subject to any disclaimer, the term of this patent is extended or adjusted under 35 U.S.C. 154(b) by 46 days.

(21) Appl. No.: 10/879,824

(22) Filed: Jun. 29, 2004

(65) Prior Publication Data

US 2005/0287497 A1    Dec. 29, 2005

(51) Int. Cl.
*A61C 8/00* (2006.01)
(52) U.S. Cl. ...................................... 433/173
(58) Field of Classification Search ........ 433/172–176; 81/121.1, 460
See application file for complete search history.

(56) References Cited

U.S. PATENT DOCUMENTS

| | | | | |
|---|---|---|---|---|
| 3,125,910 | A | * | 3/1964 | Kavalar ..................... 81/124.3 |
| 3,584,667 | A | * | 6/1971 | Reiland ........................ 81/460 |
| 4,581,957 | A | * | 4/1986 | Dossier ...................... 81/121.1 |
| 4,900,381 | A | | 2/1990 | Guenther et al. |
| 4,960,381 | A | | 10/1990 | Niznick |
| 5,030,095 | A | * | 7/1991 | Niznick ....................... 433/173 |
| 5,207,132 | A | * | 5/1993 | Goss et al. ................... 81/460 |
| 5,279,190 | A | | 1/1994 | Goss et al. |
| 5,334,024 | A | | 8/1994 | Niznick |
| 5,350,302 | A | | 9/1994 | Marlin |
| 5,388,486 | A | * | 2/1995 | Ruzicka et al. ............ 81/124.3 |
| 5,437,551 | A | | 8/1995 | Chalifoux |
| 5,549,475 | A | | 8/1996 | Duerr et al. |
| 5,782,918 | A | | 7/1998 | Klardie et al. |
| 5,810,589 | A | | 9/1998 | Michnick et al. |
| 5,823,776 | A | * | 10/1998 | Duerr et al. ................. 433/173 |
| 6,227,859 | B1 | * | 5/2001 | Sutter ......................... 433/173 |
| 6,250,922 | B1 | * | 6/2001 | Bassett et al. .............. 433/172 |
| D446,859 | S | | 8/2001 | Hurson |
| 6,315,563 | B1 | | 11/2001 | Sagar |
| 6,368,108 | B1 | | 4/2002 | Locante et al. |
| 6,394,806 | B1 | | 5/2002 | Kumar |
| 6,419,489 | B1 | | 7/2002 | Jorneus et al. |
| 6,626,911 | B1 | | 9/2003 | Engman et al. |
| 6,733,291 | B1 | | 5/2004 | Hurson |
| 2001/0034008 | A1 | * | 10/2001 | Porter et al. ................ 433/172 |
| 2002/0177105 | A1 | | 11/2002 | Engman |
| 2003/0113690 | A1 | | 6/2003 | Hollander et al. |
| 2007/0037123 | A1 | | 2/2007 | Mansueto et al. |

FOREIGN PATENT DOCUMENTS

| | | |
|---|---|---|
| DE | 103 29 207 A1 | 1/2005 |
| EP | 1 203 567 A2 | 5/2002 |
| WO | WO 99/52464 | 10/1999 |
| WO | WO 00/27300 | 5/2000 |
| WO | WO 01/49199 A2 | 7/2001 |
| WO | WO03/020154 * | 3/2003 |
| WO | WO 2004/073541 A2 | 9/2004 |

* cited by examiner

*Primary Examiner*—Cary E. O'Connor
(74) *Attorney, Agent, or Firm*—Dorsey & Whitney LLP

(57) ABSTRACT

An internal connection dental implant and implant assembly in which the implant includes a lobed configuration for installing the implant and a beveled surface positioned on the proximal side of the lobed configuration for providing stability between the implant and a corresponding abutment.

10 Claims, 7 Drawing Sheets

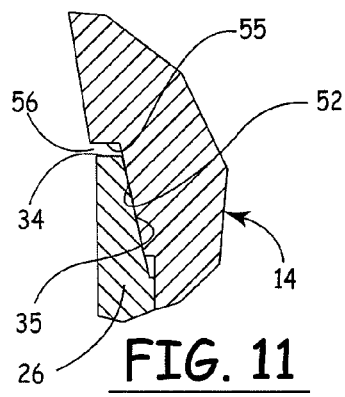
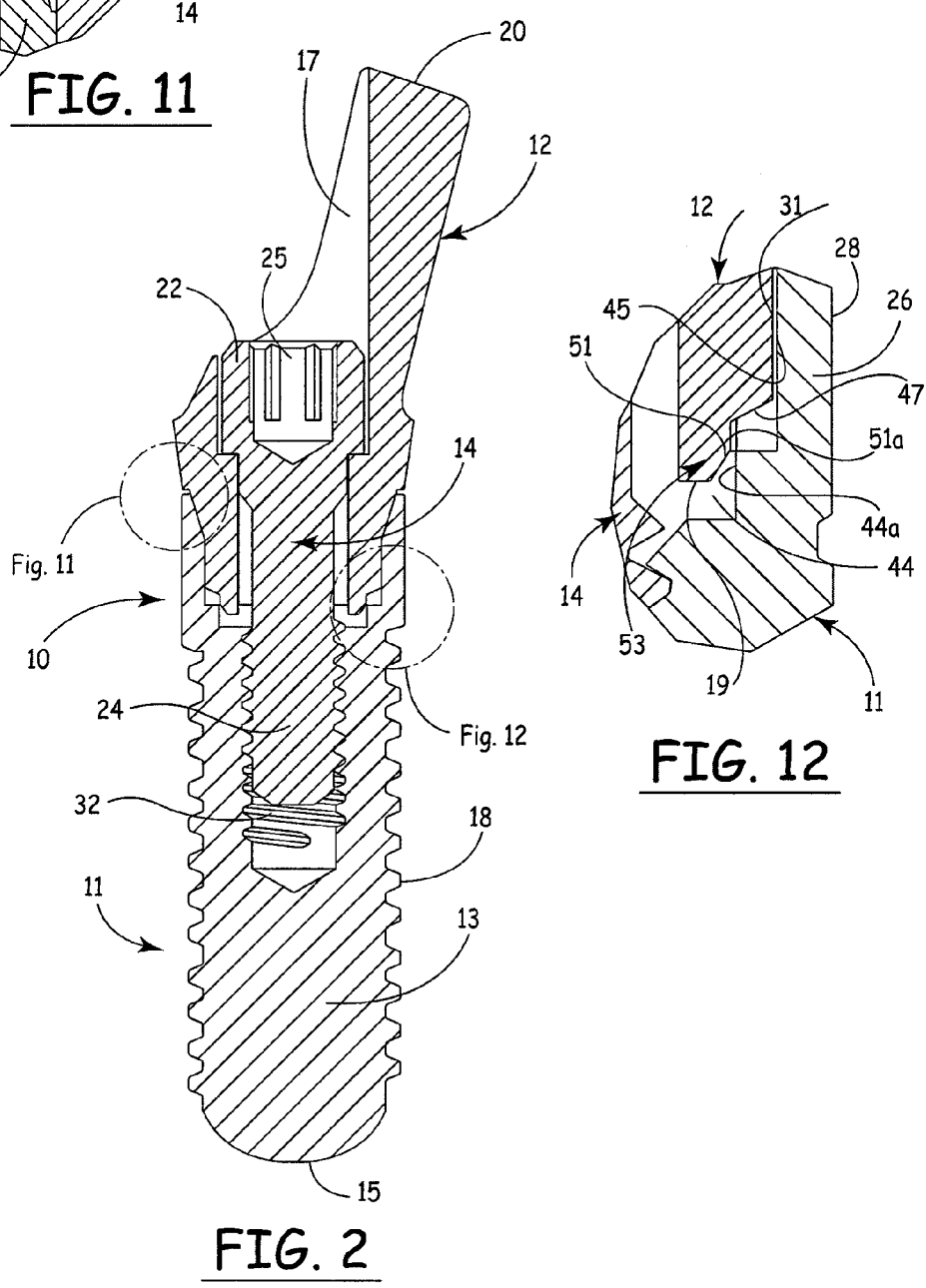
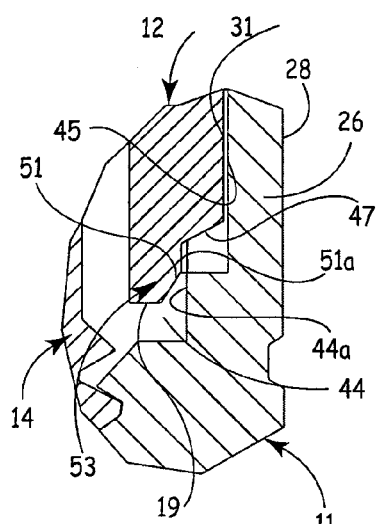

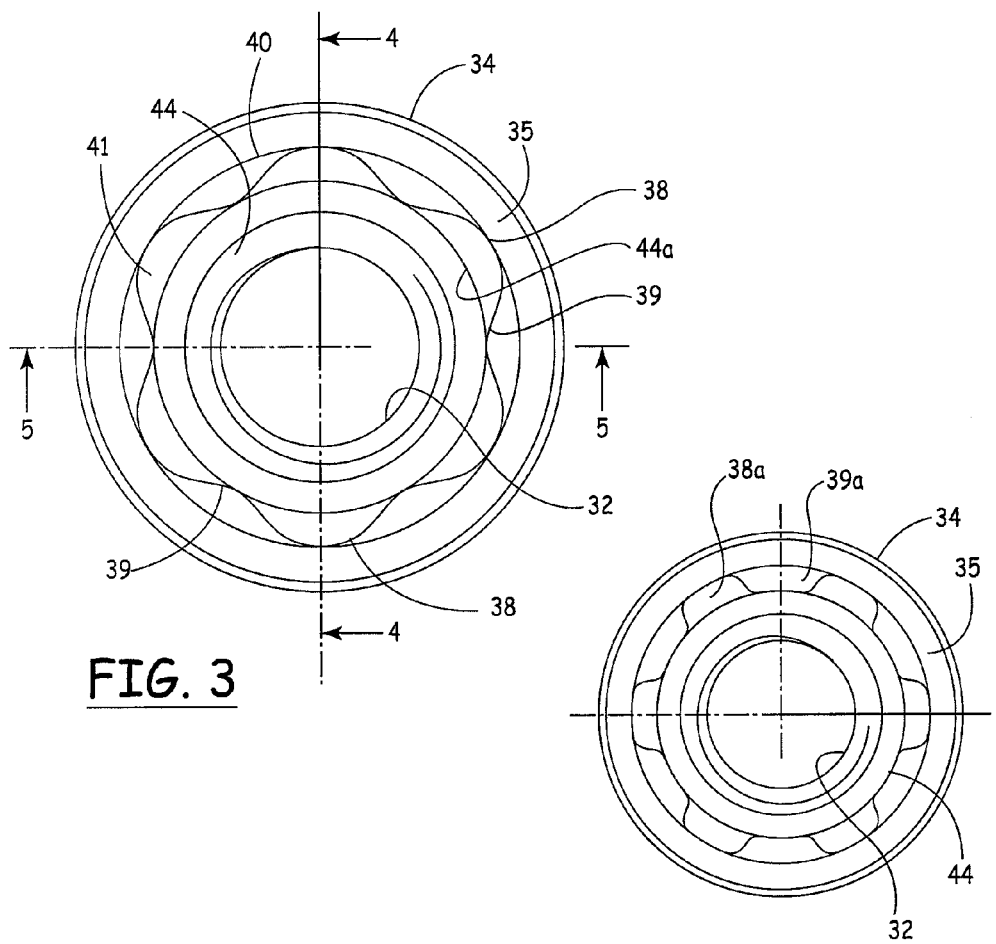
FIG. 3
FIG. 7
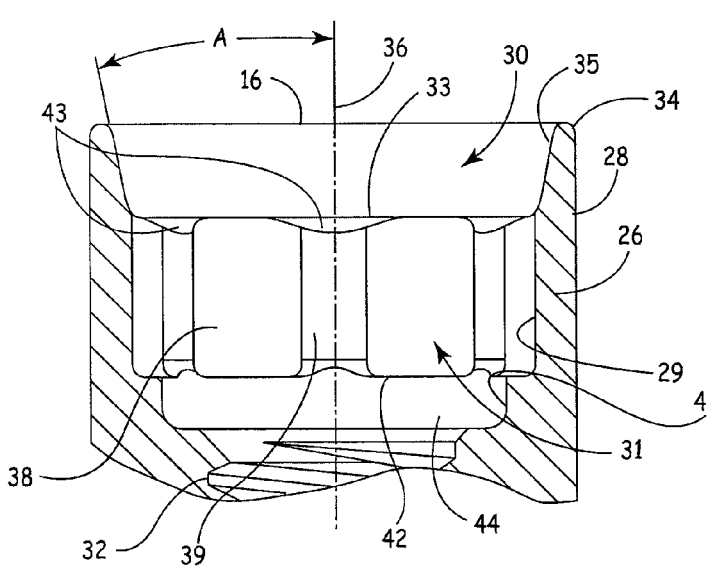
FIG. 6

INTERNAL CONNECTION DENTAL IMPLANT

BACKGROUND OF THE INVENTION

1. Field of the Invention

The present invention relates generally to the field of dental implants and more specifically to an internal connection implant. The invention also relates to the combination of an internal connection implant and a complementary abutment.

2. Description of the Prior Art

A wide variety of dental implants currently exists in the art. Such dental implants commonly include a body with external threads for mounting and retaining the implant within the patient's mouth. Installation of the implant involves rotation of the implant into a predrilled or tapped site using a drive member such as a ratchet or other rotation means. The implant also includes a drive region which may be located externally or internally. Various structures for both externally and internally driving the implant currently exist.

While many internally driven dental implants provide satisfactory torque transfer and stability between implant and abutment, implant connection failures continue to exist. Accordingly, there is a continuing need for an internal connection or internally driven implant which provides improved torque transfer and implant/abutment stability, with a structure that can also minimize implant connection failure.

SUMMARY OF THE INVENTION

The present invention relates to a dental implant and combination dental implant and abutment assembly and more specifically to an internal connection dental implant and combined internal connection implant and abutment assembly.

In general, the dental implant of the present invention includes a drive or indexing region which equalizes the stress distribution and provides for increased torque carrying capacity across the entire implant connection, thereby providing a drive means which minimizes implant connection failures and which is usable for all sizes of implants. The implant in accordance with the present invention also includes a stabilizing region which provides the implant and abutment with a highly stable connection.

In the preferred embodiment, the drive and indexing region includes a plurality of equally dimensioned and equally configured concave and convex lobes which are positioned between a minor diameter and a major diameter. This lobed configuration provides increased surface area for contact with a wrench or other drive means during installation, as well as providing an outer implant wall of sufficient thickness to improve resistance to implant connection failures, particularly when accommodating off-axis loading.

In the preferred embodiment, the stabilizing region for minimizing relative movement, so called micromotion, between the implant and a corresponding abutment, and thus improving stability between the implant and such abutment, includes a beveled surface positioned between the drive and indexing section and the proximal end of the implant. This beveled surface mates with a corresponding beveled surface of the abutment. The angle of this beveled surface is sufficient to form a friction fit so as to stabilize the interface between the implant and the abutment.

Accordingly, it is an object of the present invention to provide an internal connection dental implant and assembly facilitating improved rotational or drive torque, while at the same time minimizing failures of the implant connection during installation and use.

Another object of the present invention is to provide an internal connection dental implant and assembly which provides stability between the implant and the corresponding abutment.

These and other objects of the present invention will become apparent with reference to the drawings, the description of the preferred embodiment and the appended claims.

DESCRIPTION OF THE DRAWINGS

FIG. 2 is a view, partially in section, of the dental implant assembly of FIG. 1 in its assembled form as viewed along a plane cut through its longitudinal center.

FIG. 3 is a plan view as viewed from the proximal end of the dental implant in accordance with the present invention.

FIG. 6 is an enlarged, fragmentary view, partially in section, of the proximal end portion of the dental implant in accordance with the present invention.

FIG. 7 is a further embodiment of a lobed configuration for the dental implant in accordance with the present invention.

FIG. 11 is an enlarged, fragmentary view, partially in section, showing the relationship between the dental implant and abutment in the area of the stabilizing region.

FIG. 12 is an enlarged, fragmentary view, partially in section, showing the relationship between the dental implant and the abutment in the area of the distal end of the abutment and the drive region.

DESCRIPTION OF THE PREFERRED EMBODIMENT

The present invention is directed to a dental implant and a dental implant assembly and more specifically to an internal drive or internal connection implant and a corresponding dental implant assembly.

Figure 1:
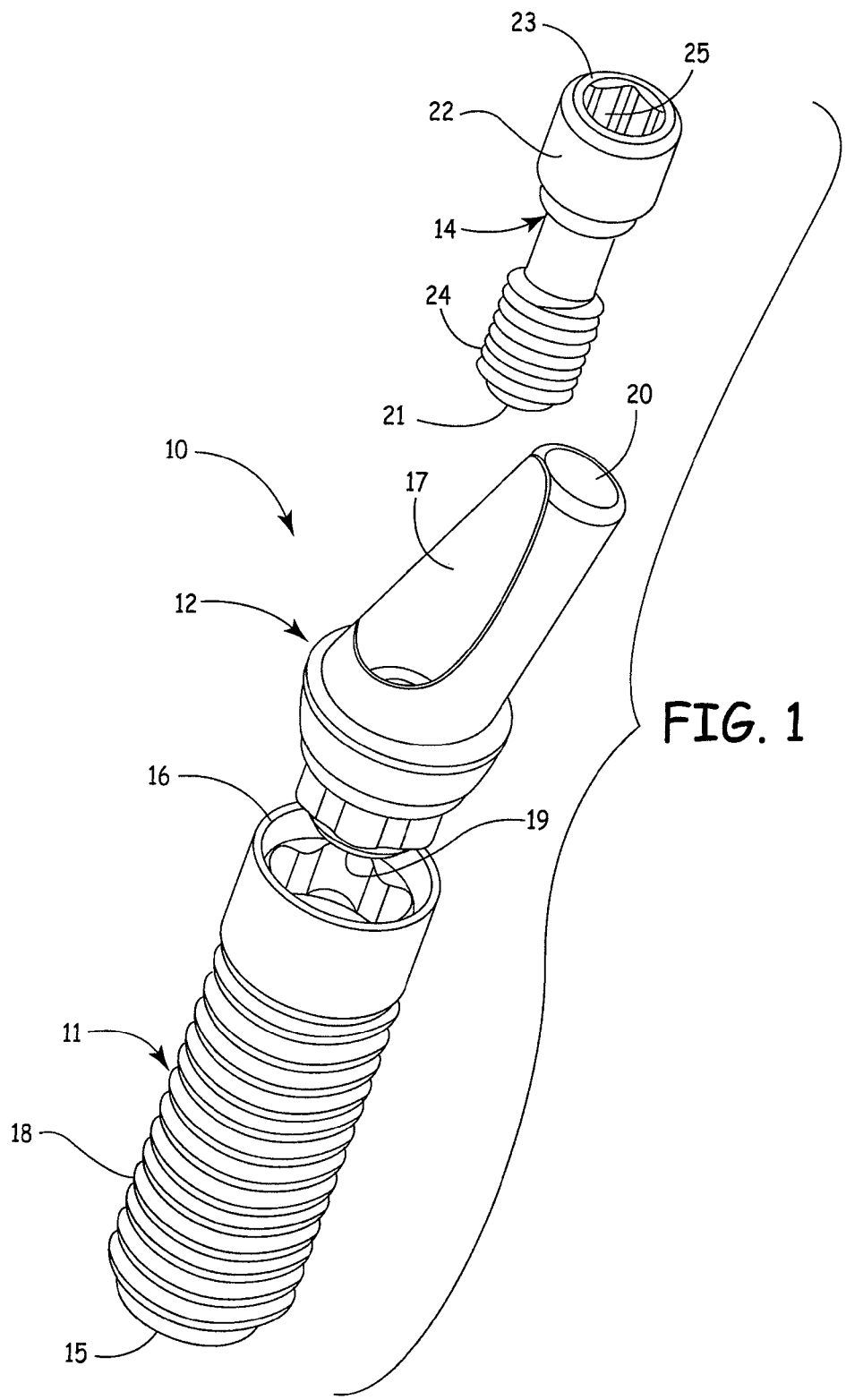
FIG. 1 is an isometric, broken apart view showing the dental implant assembly in accordance with the present invention.

Reference is first made to FIGS. 1 and 2 showing the dental implant assembly 10 in broken apart form (FIG. 1) and in assembled or connected form (FIG. 2). The dental assembly 10 includes a dental implant 11, an abutment 12 and an abutment or connection screw 14. The dental implant 11 includes a distal end 15, a proximal end 16, a body portion 13 and a plurality of external threads 18 on the body. The abutment includes a distal end 19, a proximal end 20 and an internal connection bore or opening 17. The connection screw 14 includes a distal end 21 and a proximal end 23. The screw 14 is provided with a plurality of external threads 24 near its distal end 21 and a head 22 near its proximal end 23. The head 22 is provided with wrench engaging means 25 such as an internal hex, an internal square or other driving surface.

Reference is next made to FIGS. 3, 4, 5 and 6 showing various views of the dental implant 11. The implant 11 includes a distal end 15, a proximal end 16 and an implant retaining means in the form of the external threads 18 on the outer surface of the implant. These threads 18 facilitate installation of the implant and anchor and retain the implant in the jawbone of the patient following installation. While the preferred embodiment shows the implant retaining means as comprising a single continuous thread 18 over a substantial portion of the outer surface of the implant, such retaining means can include any retaining means currently known in the art or hereinafter known in the art including, but not limited to, multiple threads, tapered threads, alternating threads of different heights, or retaining means which do not comprise threads.

Figures 4, 5:
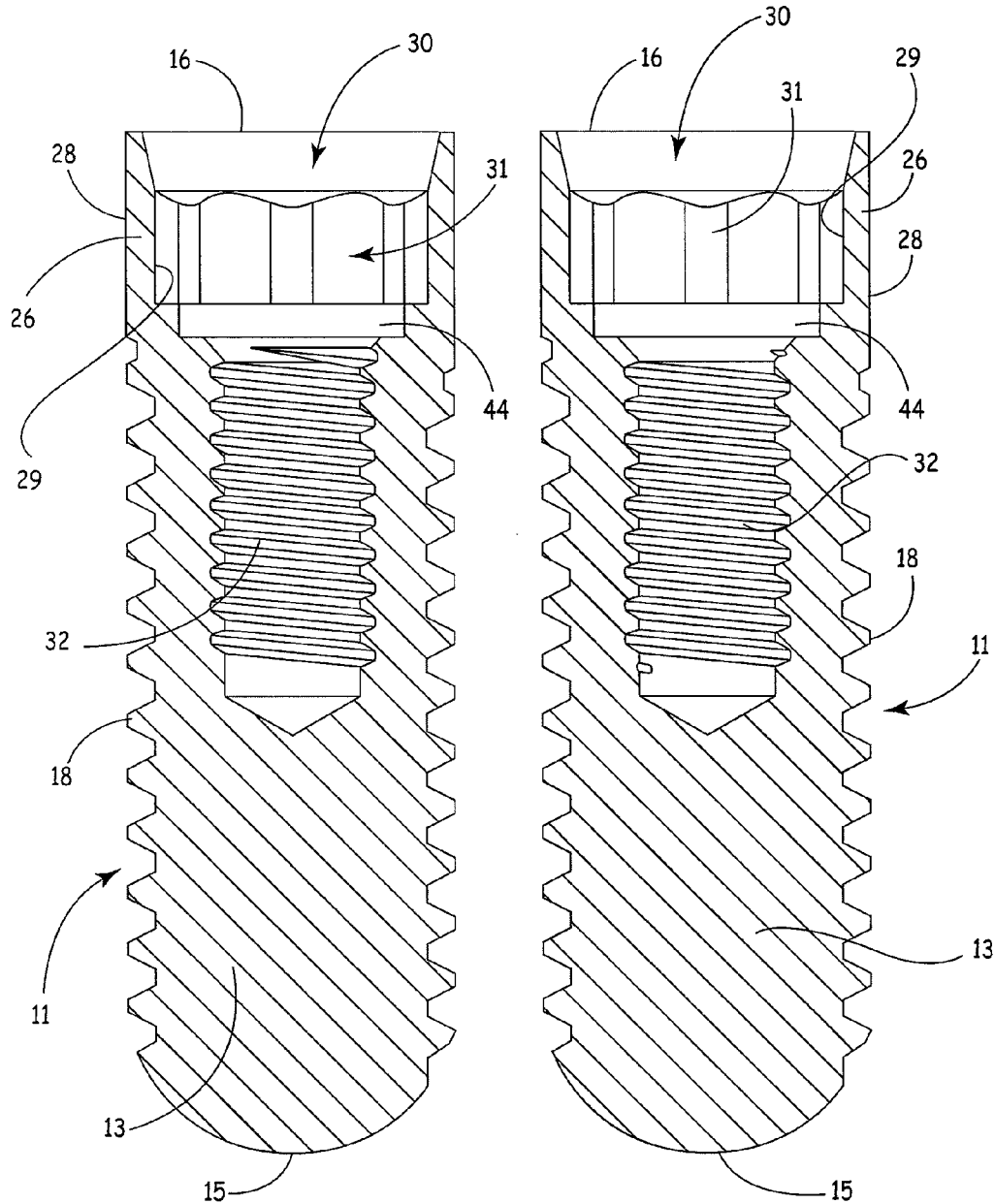
FIG. 4 is a view, partially in section, as viewed along the section line 4-4 of FIG. 3.
FIG. 5 is a view, partially in section, as viewed along the section line 5-5 of FIG. 3.

The implant 11 further includes an outer wall portion 26 located near the proximal end 16. As shown in FIGS. 4 and 5, the wall 26 is defined by an outer, unthreaded, generally cylindrical surface 28 and an inner surface 29. The surface 29 defines, and is defined by, the internal lobed configuration hereinafter described. Because the surface 29 defines both convex and concave lobes as described below, the thickness of the wall 26 will vary from thin wall sections as shown in FIG. 4 to thick wall sections as shown in FIG. 5. The outer diametrical dimension of the wall portion 26 defines the diameter of the implant in this particular region of the implant.

The interior of the implant 11 includes a stabilizing region 30, a drive and indexing region 31 and an internally threaded bore 32. The region 30 begins at or near the surface 34 and ends at the point 33 where it transitions into the drive and indexing region 31. The region 31, in turn begins at or about the point 33 and ends at its distal end 42. An accommodation region 44 is provided between the distal end 42 and the bore 32. As shown best in FIGS. 3-6, the accommodation region 44 is a generally cylindrical region having an inwardly facing cylindrical surface 44a extending from the distal end 42 toward the distal end 15 of the implant 11. As shown, the cylindrical surface 44a defines an accommodation region diameter which approximates, and is no greater than, the minor diameter 41 of the lobes 39 as discussed below. The bore 32 extends from the region 44 toward the distal end 15 of the implant 11. The internal threads of the bore 32 compliment and receive the external threads 24 of the screw 14 when the implant 11, the abutment 12 and screw 14 are in their assembled position as shown in FIG. 2.

As shown best in FIGS. 3 and 6, the proximal end 16 of the implant 11 is provided with a generally annular proximal surface 34 which defines the top of the wall portion 26. If desired, this surface may be provided with radiused edges. An interior beveled surface 35 extends from the surface 34 toward the distal end 15 of the implant. This surface 35 by itself and in combination with a corresponding surface in the abutment forms the stabilizing region 30 of the implant. The surface 35 is an internal, substantially frustoconical surface which slopes inwardly as it extends toward the distal end 15 at an angle "A" relative to the longitudinal center line 36 of the implant 11 and the combined implant/abutment assembly. The surface 35 preferably extends for a distance which is about 10 to 40% of the implant diameter in the drive or indexing region 31 as described above, more preferably about 15 to 30% of such implant diameter, and most preferably about 15 to 25% of such implant diameter.

As indicated above, the surface 35 slopes inwardly toward the distal end 15 at the angle "A". This angle can be any angle which functions to form a friction fit with a corresponding surface of the abutment as described below and thus lock and/or stabilize the implant 11 with the abutment 12. Preferably, however, this angle "A" is about 8° to about 40°, more preferably about 8° to about 30° and most preferably about 8° to about 20°. The angle "A" as shown in FIG. 6 is about 12°. Further, this angle "A" is preferably greater than the angle of a "Morse taper" and less than 45°.

The drive and indexing region 31 of the implant is comprised of a lobe configuration having a plurality of internally facing lobes which includes a plurality of outwardly extending or concave lobes 38 and a similar number of inwardly extending convex lobes 39. In the preferred embodiment, the concave lobes 38 (as well as the convex lobes 39) are angularly spaced from one another by 60°. Thus, in the preferred embodiment, there are six concave lobes 38 and six convex lobes 39. Both the concave lobes 38 and the convex lobes 39 are defined by portions of circles, with the transition between the concave lobes 38 and the convex lobes 39 being comprised of arcs tangent to the circle of each concave lobe 38 and its adjacent convex lobe 39. Still further, it is preferable for the circles which form portions of the concave lobes 38 and the circles which form portions of the convex lobes 39 to be nominally, and thus substantially, of the same radius. Specifically, while the radii of both the concave lobes 38 and the convex lobes 39 in the preferred embodiment are designed and intended to be nominally the same, the radii of one of the lobes 38 or 39 is slightly larger and the other is slightly smaller than the nominal radius to accommodate manufacturing and other tolerances and to assure clearance, when assembled.

With reference to FIG. 3, a circle intersecting the outermost points of each of the concave lobes 38 forms an outer or major diameter of the lobe configuration. A circle which intersects the innermost points of each of the convex lobes 39 forms an inner or minor diameter of the lobed configuration. Preferably, the difference between the major 40 and minor 41 diameters is kept as small as possible, while still providing sufficient torque transfer to rotate and thus install the implant into the jaw bone of a patient and to also withdraw the implant, if needed. Because the minor diameter 41 must be greater than the outermost diameter of the threaded portion 32 to allow the threaded portion 24 of the screw to pass, minimizing the diametrical difference between the major 40 and minor 41 diameters minimizes the major diameter 40 and thus maximizes the thickness of the implant wall portion 26. This in turn maximizes the strength of the implant 11 and reduces implant connection failures, both during installation and during use. This reduction in failures is particularly applicable for situations involving off-axis loading. Preferably the minor diameter 41 is about 60% to 90% of the major diameter 40, more preferably about 70% to 90% and most preferably about 80% to 90%.

As shown best in FIG. 6, the drive and indexing region 31 extends from the point 33 to its distal end 42. The point 33 defines the transition from the region 30 to the region 31 and thus the distal or ending point of the surface 35 and the beginning or proximal end of the lobe configuration. Preferably a portion of the proximal end of the region 31, and more specifically, the proximal ends of each of the convex lobes 39 is provided with an inwardly beveled (toward the distal end) surface as shown by the reference character 43 of FIG. 6. Preferably, each of the lobes 38 and 39 extends from its proximal end 33 to its distal end 42 along substantially parallel lines. Thus, the surfaces of the lobes 38 and 39 defined by the inner surface 29 of the wall 26 extend substantially parallel to the longitudinal axis 36 of the implant. Preferably, the length of the surface 29 defining the lobes 38 and 39 between the point 33 and the distal end 42 is about twice the length of the surface 35. Further, the length of the surface 29 is preferably about 20 to 60% of the implant diameter in the drive or indexing region 31, more preferably about 25 to 50% of such implant diameter and most preferably, about 30 to 40% of such implant diameter.

Accordingly, in the preferred embodiment, the drive and indexing region 31 comprises a plurality of outwardly extending concave lobes 38 and a plurality of inwardly extending or convex lobes 39. These lobes 38 and 39 are portions of circles having substantially the same or similar radii and have side walls defined by the surface 29 which are substantially parallel to each other and to the longitudinal axis 36 of the implant. The minor diameter 41 of the lobe configuration is greater than the diameter of the internally threaded bore 32 and the difference between the minor diameter 41 and the major diameter 40 should be kept as small as possible, while still providing sufficient torque transferability to install the implant and to remove it, if needed. This structure provides an outer wall 26 of increased diameter to resist, and thus reduce, implant connection failure during installation or use, regardless of the implant size and particularly when in situations involving off-axis loading.

Although the preferred lobe configuration comprises a plurality of concave lobes 38 and complimentary convex lobes 39 formed of portions of substantially equal radii, certain advantages of the present invention can also be achieved by lobed configurations which are formed of circles with unequal radii or formed of configurations other than circles. For example, convex and concave lobes which are formed as portions of ellipses are also contemplated. Such a configuration is shown in FIG. 7 in which the outwardly extending concave lobes 38a and the inwardly extending convex lobes 39a are defined by portions of ellipses. In these alternate configurations, the corresponding configurations of the loads on the abutment and the drive tools and placement heads are similarly altered.

Figure 8:
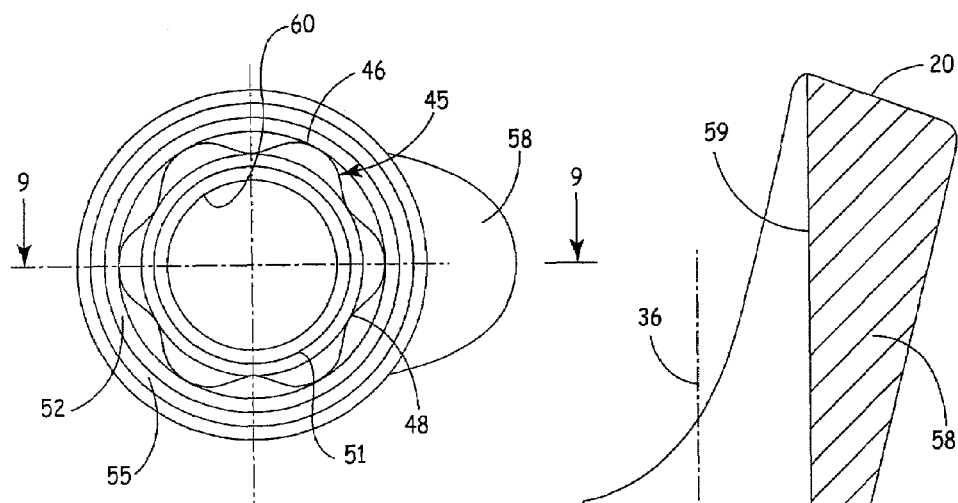
FIG. 8 is an elevational view of one embodiment of an abutment in accordance with the present invention as viewed from the distal end of the abutment.
Figure 9:
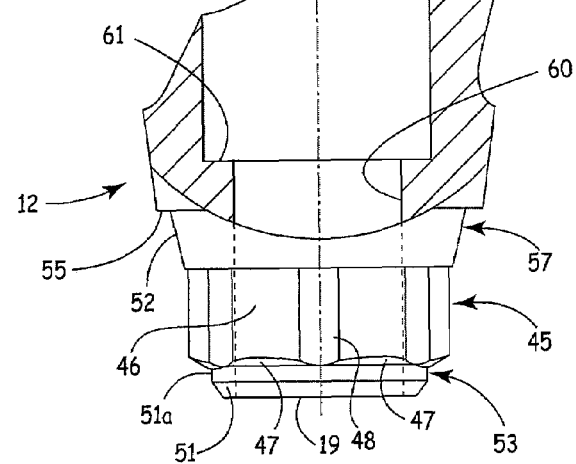
FIG. 9 is a view, partially in section, of the abutment of FIG. 8 as viewed along the section line 9-9 of FIG. 8.
Figure 10:
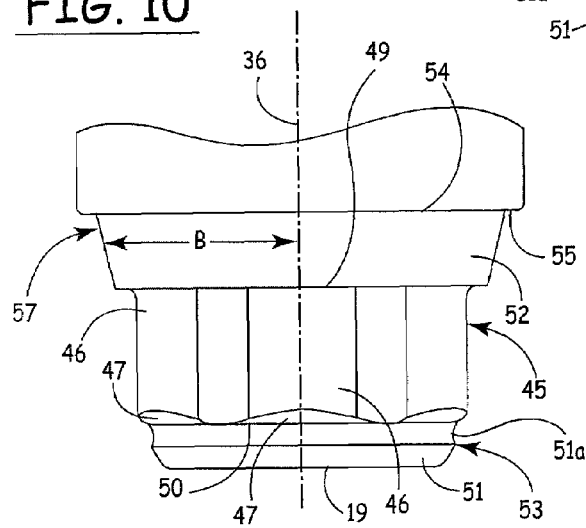
FIG. 10 is an enlarged, fragmentary side view of the distal end portion of the abutment of FIGS. 8 and 9 in accordance with the present invention.

Reference is next made to FIGS. 8, 9 and 10 showing one form of an abutment 12 usable with the implant 11. The abutment 12 includes a region 45 corresponding to the implant region 31. This region 45 includes a lobed configuration comprised of a plurality of externally facing lobes including a plurality of outwardly extending convex lobes 46 which compliment, and are designed for engagement with, the concave lobes 38, and a plurality of concave lobes 48 which compliment, and are designed for engagement with, the convex lobes 39. Thus, when assembled as shown in FIGS. 1 and 2, the lobed configuration 45 of the abutment is designed for insertion into and seating within the lobed configuration of the region 31.

The dimensions of the lobes 46 and 48, including their major and minor diameters, approximate or are slightly smaller than the major 40 and minor 41 diameters of the lobes 38 and 39. Also, like the lobed configuration of the region 31, the lobes 46 and 48 have side walls which extend substantially parallel to each other and substantially parallel to the longitudinal axis 36 of the implant assembly. Preferably, the length of the lobes 46 and 48 between their proximal end 49 and their distal end 50 is slightly shorter than the corresponding length of the lobes 38 and 39. Thus the lobes 46 and 48 are designed to slide into the lobes 38 and 39, respectively, in relatively close tolerances. Also, as shown best in FIGS. 9 and 10, a portion of the distal end of the lobed configuration 45, and more specifically, the distal ends of each of the convex lobes 46 is provided with an inwardly beveled (toward the distal end) surface as shown by the reference character 47.

The distal end 19 of the abutment 12 includes and is defined by a lead-in portion or region 53. As shown best in FIGS. 8, 9, 10 and 12, the region 53 includes a cylindrical section defined by the outwardly facing cylindrical surface portion 51a and a frustoconical section defined by the beveled lead-in surface portion 51. As shown best in FIG. 12, the outer diameter of the cylindrical surface 51a is less than the inner diameter of the accommodation region 44 defined by the surface 44a. This lead-in surface 51 helps to guide the lobed configuration 45 of the abutment 12 into the lobed configuration region 31 of the implant 11. When the abutment and implant are in assembled form as shown in FIG. 2, the lead-in region 53 and the surface 51 are accommodated within the accommodation section 44 (FIGS. 2, 6 and 12).

A locking or stabilizing portion 57 of the abutment 12 is positioned adjacent to the proximal end 49 of the lobed configuration 45 and extends from that end 49 to the end 54. This portion 57 includes a beveled surface 52 which bevels inwardly from its proximal end 54 toward the end 49. This surface 52 is an external, substantially frustoconical surface which forms an angle "B" with the center line 36 of the implant and the implant assembly when assembled. Preferably, this angle "B" is the same as angle "A", however, certain advantages of the present invention can be achieved with angles "A" and "B" which are different from one another. Preferably, however, the angle "B" is about 8 to 40°, more preferably about 8 to 30° and most preferably about 8 to 20°.

Extending outwardly from the proximal end 54 of the surface 52 abutment is a shoulder which includes a distal facing surface 55. This surface 55 has a generally annular configuration with radiused corners. In some abutment configurations, the shoulder can be eliminated.

When the abutment 12 is assembled within the implant 11, as shown best in FIGS. 2 and 11, the surfaces 52 and 35 engage one another in a friction fit engagement. The friction fit between the beveled surfaces 52 and 35 provides a tapered locking engagement between these two surfaces. This provides stability between the abutment 12 and the implant 11 to preclude or reduce any rocking or micromotion between the abutment 12 and the implant 11.

The abutment 12 further includes a main body portion 58 between the section 57 and the proximal end 20. This body 58 supports the prosthetic tooth or other appliance. A throughhole or bore 17 extends through a portion of the body 58 and through the stabilizing portion 57, the lobed configuration 45 and the lead-in region 53. The throughhole 17 is defined at its proximal end by the bore 59 and at its distal end by the bore 60. The bores 59 and 60 are joined by the abutment screw support shoulder 61.

When the abutment is assembled and installed in a patient as shown in FIG. 2, the abutment screw 14 extends through the bore 17, with its external threads 24 engaging the internal threads 32 of the implant 11. The head 22 of the screw 14 includes a shoulder portion which mates with and seats against the shoulder 61 of the abutment. As the abutment screw 14 is advanced against the shoulder 61, the surface 52 is forced into and against the surface 35, with the lobed configuration 45 of the abutment positioned within the lobed configuration 31 of the implant.

The embodiment of the abutment shown in FIGS. 8, 9 and 10 is a pre-angled abutment which results in off-axis loading. Thus, the throughhole 17 is aligned with the abutment sections 53, 45 and 57 and the longitudinal axis 36 of the implant when assembled, but is not fully aligned with the body portion 58 of the abutment. Abutments can assume various configurations, including pre-angled abutments with various angles and straight abutments which are not provided with or intended for off-axis mounting. In these straight abutments, the throughhole 17 would extend through the distal end 20 of the abutment.

Figure 13:
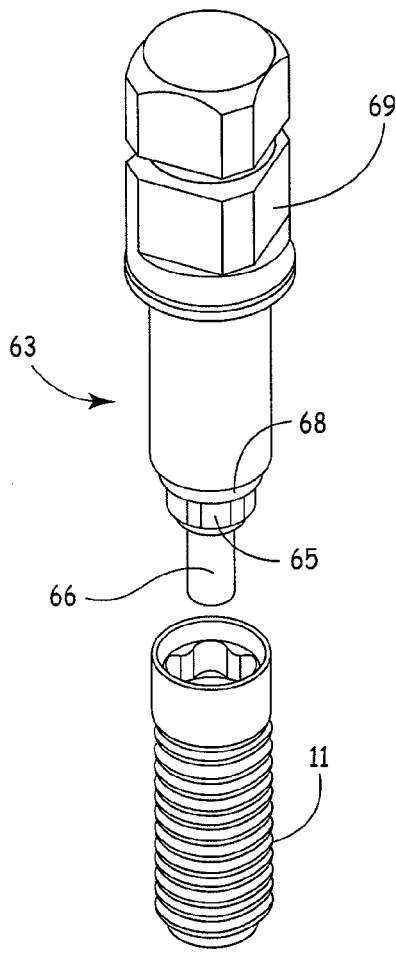
FIG. 13 is an isometric, broken apart view of a direct drive tool for installing the dental implant in accordance with the present invention.
Figure 14:
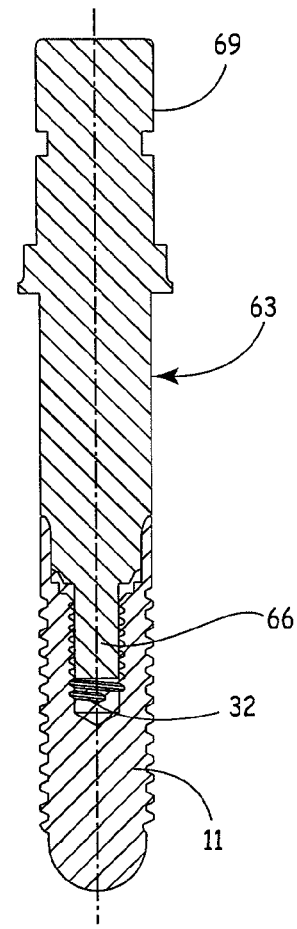
FIG. 14 is a view, partially in section, of the tool of FIG. 13 being used to rotate an implant.
Figure 15:
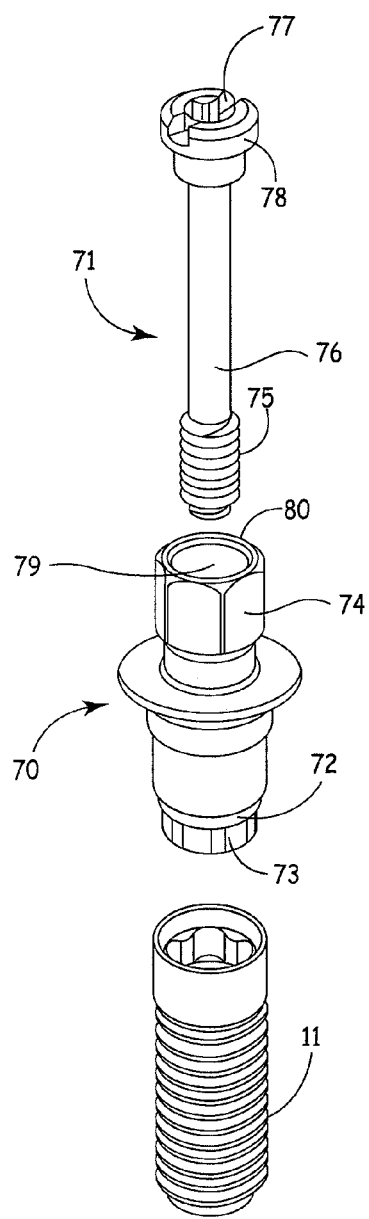
FIG. 15 is an isometric, broken apart view of a fixture mount assembly for installing the dental implant in accordance with the present invention.
Figure 16:
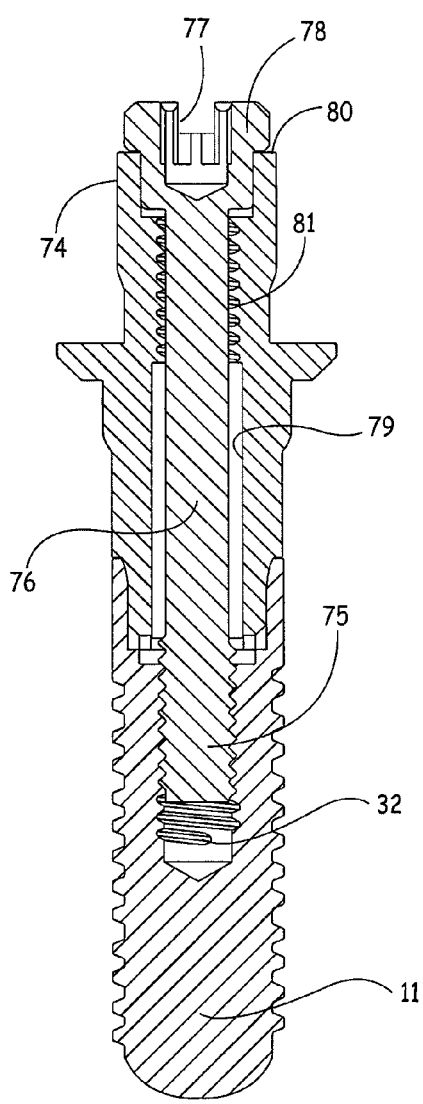
FIG. 16 is a view, partially in section, of the fixture mount assembly of FIG. 15 in preassembled form within an implant.
Figure 4:
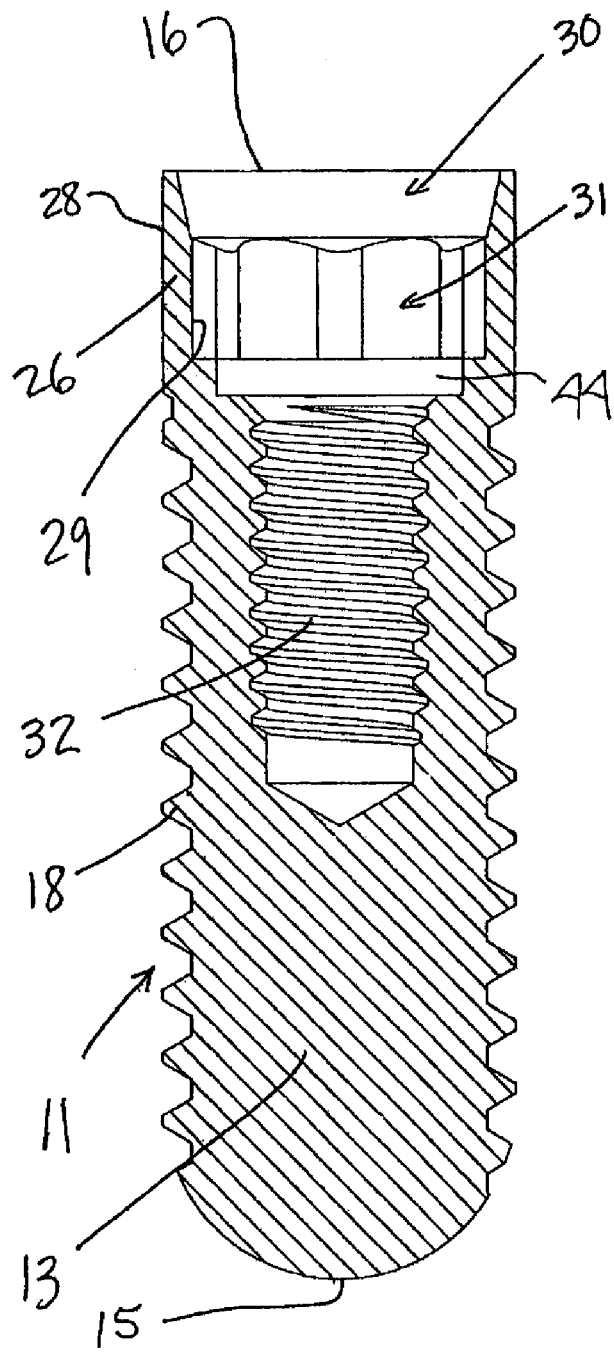
Figure 5:
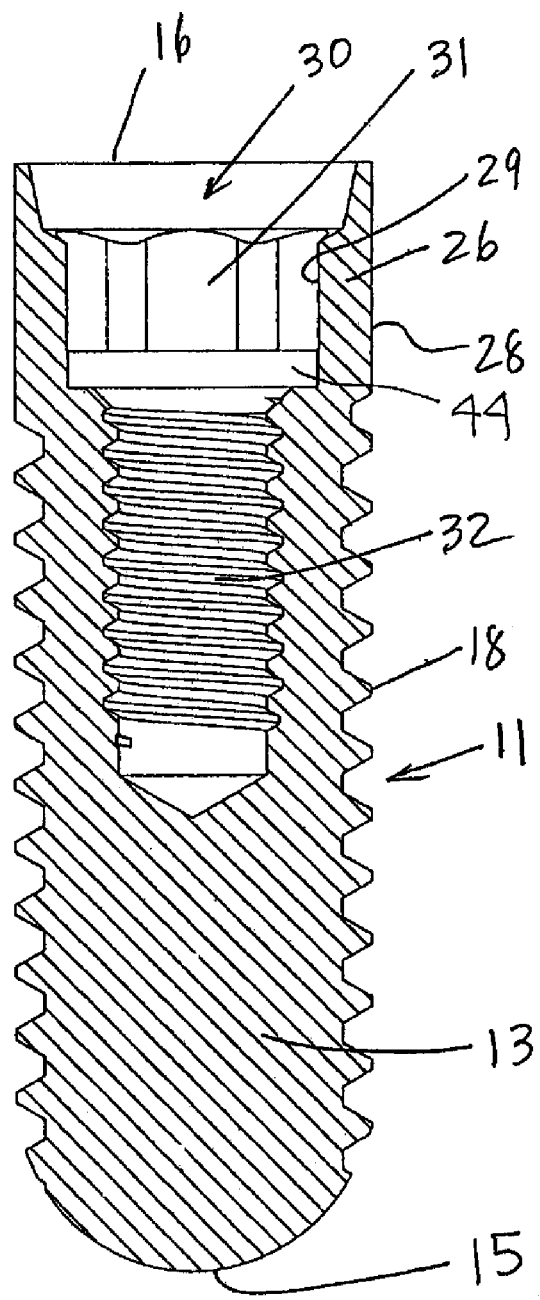

FIGS. 13-16 show two embodiments of drive means for installing the implant 11. Specifically, FIGS. 13 and 14 illustrate a direct drive embodiment, while FIGS. 15 and 16 illustrate an implant with a preassembled fixture mount.

With reference to FIGS. 13 and 14, the direct drive includes a guide portion 66, a drive portion 65, a surface portion 68 and a rotation region 69. The guide portion 66 comprises a generally cylindrical, unthreaded structure extending generally parallel to the longitudinal axis of the drive member 63. The region 65 comprises a lobed configuration substantially matching the lobed configuration 45 of the abutment (FIG. 9) so that when the drive member 63 is inserted into the implant 11 and rotated, the lobed configuration 65 mates with and engages the lobed configuration 31 in driving relationship. The rotation portion 69 may comprise a hex, a square or any other means to which a motorized or non-motorized instrument or the like can be applied to rotate the drive member 63 and thus the implant 11.

FIGS. 15 and 16 show a preassembly comprising an implant and an accompanying fixture mount assembly. The assembly includes the mount 70 and the retaining screw 71. The adapter includes a lobed configuration 73 substantially matching the lobed configuration 45 of the abutment (FIG. 9) so that when the mount 70 is inserted into the implant 11 in its assembled form as shown in FIG. 16, the lobed configuration 73 mates with and engages the lobed configuration 31 in driving relationship. A rotation member 74 is formed at the proximal end of the adapter 70 and may be a hexagonal shape as shown, a square, or any other shape that will accommodate a drive member. The mount 70 includes a central bore or throughhole 79 to receive the screw 71. The bore 79 includes an internally threaded portion 81 to capture the screw 71 within the adapter 70. The screw includes an externally threaded portion 75 at its distal end, an elongated shaft 76 and a head 78 with a slot 77 or other rotation means.

When assembled with an implant 11, as shown in FIG. 16, the lobed portion 73 is inserted into the open end of the implant 11 to mate with the corresponding lobed portion 31 of the implant. The screw 71 is then inserted through the open end of the bore 79 and the distal end is threaded into the internal threads 32 of the implant 11. The screw 71 is tightened until the lower surface of the mount 78 tightly engages the proximal end 80 of the mount, thereby firmly securing the fixture mount assembly within the implant 11.

Having described the structure of the dental implant and dental implant assembly of the present invention, its installation can be best understood as follows. First, after preparing the implant site within the patient's mouth, the implant is installed by rotating the same, either with a direct drive member 63 such as is shown in FIGS. 13 and 14 or with a preassembled fixture mount as shown in FIGS. 15 and 16. After the implant is installed to the desired installation depth, the drive member 63 or the fixture mount assembly is removed from the implant. The abutment is then positioned within the open end of the implant, with the lobed configuration 45 and surface 52 of the abutment being positioned within and engaging the lobed configuration 31 and surface 35 of the implant. The abutment screw 14 is then inserted into the open end of the bore 17 and rotated by a ratchet or other rotation tool known in the art. Rotation of the screw 14 forces the beveled surface 52 against the beveled surface 35 forming a tight friction fit. This provides stability between the abutment and the implant.

Although the description of the preferred embodiment has been quite specific, it is contemplated that various modifications could be made without deviating from the spirit of the present invention. Accordingly, it is contemplated that the scope of the present invention be dictated by the appended claims rather than by the description of the preferred embodiment.

The invention claimed is:

1. A dental implant comprising:
   a body having a longitudinal axis, a proximal end and a distal end;
   implant retaining means provided on an external portion of said body;
   an internal bore provided within a portion of said body, said internal bore having a proximal end at the proximal end of said body and a distal end;
   an internally facing surface having a proximal end and a distal end, said surface extending from near the proximal end of said internal bore toward the distal end of said internal bore, said surface being beveled inwardly toward its distal end;
   an internally facing drive region positioned within said internal bore between the distal end of said surface and the distal end of said internal bore, said drive region including a plurality of concave lobes and a plurality of convex lobes alternating with said concave lobes, the radially outermost points of each of said convex lobes lying on a circle defining a major diameter and the radially innermost points of each of said concave lobes lying on a circle defining a minor diameter, wherein at least a portion of each of said concave lobes has a circular configuration and at least a portion of each of said convex lobes has a circular configuration;
   a cylindrical accommodation region positioned within said internal bore and between the distal end of said drive region and the distal end of said internal bore, said accommodation region includes an inwardly facing cylindrical surface defining an accommodation region diameter no greater than said minor diameter; and
   an internally threaded portion positioned within said internal bore and between said accommodation region and the distal end of said body, said threaded portion having a diameter less than said accommodation region diameter.

2. The dental implant of claim 1 wherein the entirety of each of said plurality of convex lobes is defined by a circular configuration segment and the entirety of each of said plurality of concave lobes is defined by a circular configuration segment.

3. The dental implant of claim 2 wherein the circular configuration of each of said concave lobes is comprised of a single circular segment and the circular configuration of each of said convex lobes is comprised of a single circular segment.

4. The dental implant of claim 3 wherein the diameter of the single circular segment of each of said concave lobes is the same as the diameter of the single circular segment of each of said convex lobes.

5. The dental implant of claim 1 wherein said accommodation region diameter is the same as said minor diameter.

6. The dental implant of claim 1 wherein the entirety of each of said concave lobes and said convex lobes is comprised of a circular configuration.

7. A dental implant assembly comprising:
   a dental implant comprising:
      a body having a longitudinal axis, a distal end and an open proximal end;
      implant retaining means provided on an external portion of said body;
      an internal bore provided within a portion of said body, said internal bore having a proximal end at the open proximal end of said body and a distal end;
      an internally facing drive region positioned within said internal bore and opening toward the proximal end of said internal bore, said drive region including a plurality of concave lobes and a plurality of convex lobes alternating with said concave lobes, the radially outermost points of each of said convex lobes lying on a circle defining a major diameter and the radially innermost points of each of said concave lobes lying on a circle defining a minor diameter, wherein at least a portion of each of said concave lobes has a circular configuration and at least a portion of each of said convex lobes has a circular configuration;
      a cylindrical accommodation region positioned within said internal bore and between the distal end of said drive region and the distal end of said internal bore, said accommodation region includes an inwardly facing cylindrical surface defining an accommodation region diameter no greater than said minor diameter; and
      an internally threaded region at the distal end of said internal bore, said threaded portion having a diameter less than said accommodation region diameter; and an abutment selectively connectable to said dental implant and comprising:
      a proximal end and a distal end;
      an abutment surface corresponding to and adjacent to said drive region when said dental implant and said abutment are connected, said abutment surface including a plurality of convex lobes and a plurality of concave lobes corresponding respectively to said concave and convex lobes of said drive region;
      a prosthesis mounting portion;
      a central bore extending through at least a portion of said prosthesis mounting portion; and
      an abutment screw extending through said central bore and into said internally threaded region when said dental implant and said abutment are connected.

8. The dental implant assembly of claim 7 wherein said lead-in diameter is less than said accommodation region diameter.

9. The dental implant apparatus of claim 7 wherein said drive region includes an inwardly beveled surface at its proximal end.

10. The dental implant apparatus of claim 9 including a beveled surface.

* * * * *

UNITED STATES PATENT AND TRADEMARK OFFICE
CERTIFICATE OF CORRECTION

PATENT NO. : 7,249,949 B2  Page 1 of 1
APPLICATION NO. : 10/879824
DATED : July 31, 2007
INVENTOR(S) : Robert D. Carter It is certified that error appears in the above-identified patent and that said Letters Patent is hereby corrected as shown below:

| Column | Line |  | Should Read |
|---|---|---|---|
| 8 | 49 | "convex" | -- concave -- |
| 8 | 51 | "concave" | -- convex -- |
| 9 | 34 | "convex" | -- concave -- |
| 9 | 36 | "concave" | -- convex -- |

Signed and Sealed this

Twenty-second Day of July, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,249,949 B2 | Page 1 of 2 |
| APPLICATION NO. | : 10/879824 | |
| DATED | : July 31, 2007 | |
| INVENTOR(S) | : Robert D. Carter | |

It is certified that error appears in the above-identified patent and that said Letters Patent is hereby corrected as shown below:

Delete drawing sheet 4 of 7 and substitute replacement Sheet 4 of 7, which reflects the correction to Figure 5.

Signed and Sealed this

Fifteenth Day of September, 2009

David J. Kappos
*Director of the United States Patent and Trademark Office*